United States Patent [19]

de Silva et al.

[11] Patent Number: 4,836,039

[45] Date of Patent: Jun. 6, 1989

[54] METHOD AND APPARATUS FOR INTRODUCTION OF A PARTICULATE SAMPLE FOR ANALYSIS

[75] Inventors: K. Nimalasiri de Silva, Ottawa; Roger Guevremont, Bedford, both of Canada

[73] Assignee: Canadian Patents & Development Limited, Ottawa, Canada

[21] Appl. No.: 95,123

[22] Filed: Sep. 10, 1987

[51] Int. Cl.$^4$ .............................................. G01N 1/00
[52] U.S. Cl. .............................. 73/864.81; 250/288; 356/36; 406/93; 406/134
[58] Field of Search ........... 73/864.81, 864.82, 864.83, 73/864.84, 864.85; 250/288, 288 A; 356/315, 316, 36; 406/93, 94, 134, 146

[56] References Cited

U.S. PATENT DOCUMENTS

| | | | |
|---|---|---|---|
| 2,836,097 | 5/1958 | Garman | 356/315 |
| 3,976,332 | 8/1976 | Fabel | 406/14 |
| 4,451,184 | 5/1984 | Mitchell | 406/93 |
| 4,662,789 | 5/1987 | Fassbinder | 406/93 |
| 4,687,929 | 8/1987 | Browner et al. | 250/288 |

FOREIGN PATENT DOCUMENTS 1166495 10/1969 United Kingdom .................. 406/14

Primary Examiner—Stewart J. Levy
Assistant Examiner—Robert P. Bell
Attorney, Agent, or Firm—Ronald G. Bitner

[57] ABSTRACT

A method and apparatus for delivering a particulate sample to an analyzing device such as a flame or plasma spectrometer, which provides relatively uniform, continuous and controlled delivery of a sample and allows sample changing without disrupting the operation of the analyzing device.

5 Claims, 1 Drawing Sheet

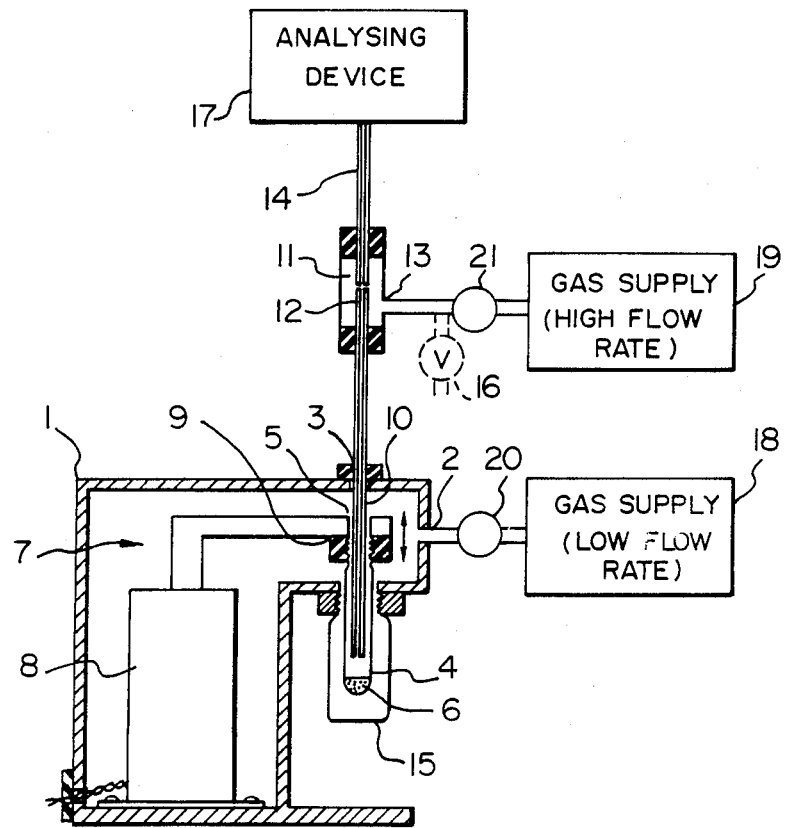

METHOD AND APPARATUS FOR INTRODUCTION OF A PARTICULATE SAMPLE FOR ANALYSIS

BACKGROUND OF THE INVENTION

The invention relates to a method and apparatus for introducing a particulate solid sample for analysis, and particularly for flame or plasma spectroscopy.

A number of problems have impeded the development of practical methods for flame or plasma analysis of solid samples. The sample must be introduced uniformly to the plasma to minimize variations in plasma characteristics, such as temperature, available energy, etc. Uniform sample delivery is required for most commercially available instrumentation for wavelength scans, background corrections, and integration times of sufficient duration to maximize sensitivity. Sample flow must be controlled to avoid overloading the analyzing device. Sufficient mass must be analysed to avoid problems related to inhomogeneity.

Several approaches for delivering solid samples for direct analysis by flame or plasma have been proposed. The direct introduction of powders into a flame or inductively coupled plasma by a fluidized-bed approach has also been proposed.

In the prior system the same injector gas entrains the sample, and delivers it to the plasma. The gas flow rate is chosen to be compatible with the requirements of the analyzing device, rather than a flow which would result in an optimum fluidized bed. With the prior system the sample flow is difficult to control and cannot be maintained uniform over a period of time. Because of this, quantitative measurements can usually be done only by introducing the total (weighed) sample. Also, with the prior system, samples cannot be changed without disrupting the plasma.

An object of the present invention is to allow continuous, uniform, and controlled delivery of particles for flame or plasma analysis.

Another object is to allow independent control of sample introduction, or sample change without disrupting the flame or plasma.

It has been found that the above objectives can be met by providing two stages of flow comprising a first stage of relatively low flow for entraining the fluidized solid particles in controlled amounts and a second stage of relatively high uniform flow as required by the analyzing device.

The present invention provides an apparatus for introducing a particulate sample to an analyzing device comprising: an enclosure having an inlet for a first carrier gas, and an outlet for gas entrained sample particles; a sample container disposed within the enclosure, said container having an opening for receiving the first carrier gas, supplied at a relatively low flow rate to the enclosure; agitating means for fluidizing a sample contained by the sample container; conduit means communicating with the interior of the sample container, said conduit defining the outlet from the enclosure of a sample entrained by carrier gas supplied to the container; and a combining chamber connected to said conduit, said combining chamber including an inlet for receiving a second carrier gas, of relatively high flow rate, and an outlet for connection to an analyzing device.

The present invention also provides a method for introducing a particulate sample to an analyzing device comprising: fluidizing the sample by agitation; passing a first carrier gas of relatively low substantially uniform flow rate through the fluidized sample for entrainment of a portion of the sample; and combining the first carrier gas and entrained sample with a second carrier gas having a relatively high substantially uniform flow rate so that the combined flow has a high substantially uniform flow rate that is compatible with the requirements of the analyzing device.

BRIEF DESCRIPTION OF THE DRAWING

The DRAWING is a partly schematic, partly cross-sectional view of an embodiment of the present invention.

DESCRIPTION OF THE PREFERRED EMBODIMENT

Referring to the drawing, the apparatus of the present invention comprises a substantially gas-tight enclosure 1 having an inlet 2 for a first carrier gas and an outlet 3 for the sample entrained by the carrier gas. Within the enclosure 1, is a sample container 4 having an opening 5 for receiving carrier gas supplied to inlet 2. The sample 6 is fluidized by agitating means 7 shown as a solenoid 8 and connecting means 9 for supporting the container 4.

The gas entrained sample exits the enclosure through conduit 10 which communicates with the interior of the container 4. The conduit 10 connects with the combining chamber 11 at inlet 12. The chamber 11 includes an inlet 13 for supplying a second carrier gas and outlet 14 for delivery to the analyzing device.

Delivery of the first and second carrier gas is regulated by suitable flow controlling means 20 and 21 from the respective source 18 and 19.

Preferably, the enclosure 1 is provided with a removable portion 15 to facilitate access to the sample container 4 inside the enclosure for changing the sample.

A valve 16 may be used to reduce the gas flow rate while the sample is being changed.

In operation, the carrier gas supplied at inlet 2 pressurizes the enclosure 1, enters the sample container 4 through opening 5 and exits via the conduit 10. The sample 6 is fluidized by agitating the container 4 by means of the solenoid 8. The carrier gas that exits through conduit 10 entrains a portion of the fluidized sample on a continuous basis. At chamber 11, the 1st carrier gas containing the particles is combined with a second carrier gas supplied at inlet 13 at a relatively high and uniform flow rate. Sample delivery can be initiated or terminated by control of the agitating means. Preferably, before beginning of agitation of the container for sample introduction, the operation includes a short period of time for stabilization of the gas flows at desired values after changing of sample and closing of valve 16.

The rate of sample flow can be controlled by changing the frequency of vibration of the container or by controlling the flow rate of gas to inlet 2. Selection of values for the frequency of vibration, and flow rate of gas to inlet 2 is made to obtain a suitable fluidized bed and a uniform flow rate of sample. The gas flow requirements of the analyzing device do not influence selection of these values. Additional gas, as needed to bring the total flow up to that required by the analyzing device is added through inlet 13.

The flow of gas entering inlet 2 may be adjusted without altering the total flow to the analyzing device.

The sum of flows through inlet 2 and inlet 13 is maintained constant with a controlling means 20 and 21. The preferred control means are mass flow controllers.

Suitable flow rates for the 1st carrier gas entering inlet 2 appear to be in the range of 15 to 100 ml/min. The optimum flow rate of the 1st carrier gas will also depend on the nature of the particles. The flow rate of the 2nd carrier gas supplied at inlet 13 is determined by the requirements of the analyzing device. Analysis with flame or plasma emission spectrometry may require total gas flows from 300 to over 1000 cc/min.

The frequency of agitation of the sample container will depend on the physical nature of the sample material. Suitable frequencies for oscillation of the agitation means appears to be 1 to 20 Hz.

The present arrangement allows the gas flow to the analyzing device to be maintained independent of the sample delivery, or changing of the sample. The sample delivery can be started, or stopped by control of the agitating means (and rate controlled by its frequency), and gas flows to inlets 2 and 13 altered without terminating operation of the analyzing device.

The sample is changed by removing cover 15, and detaching the sample container 6 from member 9. This operation has minimum effect on the analyzing device since a large portion of the gas which enters through inlet 13 will continue to pass through conduit 14. Air cannot enter conduit 10 due to the higher than atmospheric pressure inside combining chamber 11, and therefore analyzing devices such as rf plasmas will function normally during the change of sample. In addition the gas passing down through conduit 10, plus the gas entering through inlet 2, will prevent air from entering the enclosure 1.

When the cover 15 is removed, the sudden reduction of pressure inside the enclosure will divert enough of the flow downwards through the conduit 10 which may cause the sample to be blown out of container 4. To prevent this, valve 16 can be opened prior to opening of the cover 15, to divert most of the "high flow" gas to the outside and to release the pressure inside the enclosure 1 without a high downward flow through conduit 10. When the cover is opened the flow down the conduit 10 will be small enough not to disturb the sample.

The moving parts, including agitating means, and the sample container 4, are all contained within the enclosure 1, and removable portion or cover 15. Preferably, as is shown in the drawing, the outlet conduit 10 is dimensioned for clearance with the container 4 to define the inlet 5 for the carrier gas. This arrangement prevents any volume displacement changes during agitation and therefore avoids pulsing of the flow due to pressure fluctuations. This arrangement also provides a convenient way of changing the sample.

When very low frequency of vibration of sample agitation is used, there may be an undesirable fluctuations of the flow of particles corresponding to the frequency. This variation can be reduced by increasing the length of the conduit (capillary) 14 between the combining chamber 11 and the analyzing device 17. Normally however, a short conduit is preferred to avoid particle deposition and possible contamination in subsequent analysis.

The present invention may be useful for particulate sample introduction for various analytical systems such as ICP (Inductively Coupled Plasma) spectrometry, flame atomic absorption spectrometry, flame atomic emission spectrometry, direct current plasma atomic emission spectrometry, or microwave plasma emission spectrometry.

We claim:

1. An apparatus for introducing a particulate sample to an analyzing device comprising:
    a substantially gas-tight enclosure having an inlet for a first carrier gas, and an outlet for gas entrained sample particles;
    a sample container disposed within the enclosure, said container having an opening for receiving said first carrier gas supplied at a relatively low flow rate to the enclosure;
    agitating means for fluidizing a sample contained by the sample container;
    support means connected with the agitating means for removably attaching the sample container thereto;
    conduit means communicating with the interior of the sample container, said conduit defining the outlet for the enclosure of a sample entrained by carrier gas supplied to the container; and
    a combining chamber connected to said conduit, said combining chamber including an inlet for receiving a second carrier gas, of relatively high flow rate, and an outlet for connection to an analyzing device.

2. The apparatus of claim 1, further comprising opening means in the enclosure for providing access to the sample container.

3. The apparatus of claim 1 further comprising flow controlling means for providing a uniform predetermined flow rate for each of the first carrier gas and the second carrier gas.

4. The apparatus of claim 1 wherein the agitating means are disposed within the enclosure.

5. A method for introducing a particulate sample to an analyzing device comprising
    fluidizing the sample by agitation;
    passing a first carrier gas of relatively low substantially uniform flow rate through the fluidized sample for entrainment of a portion of the sample; and
    combining the first carrier gas and entrained sample with a second carrier gas having a relatively high substantially uniform flow rate so that the combined flow has a high substantially uniform flow rate that is compatible with the requirement of the analyzing device, and
    providing a continuing flow of carrier gas while changing the sample so as to avoid disrupting the operation of the analyzing device.

* * * * *